(12) United States Patent
Aruga et al.

(10) Patent No.: US 7,741,041 B2
(45) Date of Patent: Jun. 22, 2010

(54) DIAGNOSTIC ANALYTICAL METHOD UTILIZING DNA CHIPS WITH THIN-FILM TRANSISTOR (TFT) ELEMENTS

(75) Inventors: Hisashi Aruga, Fujimi (JP); Tatsuya Shimoda, Fujimi (JP)

(73) Assignee: Seiko Epson Corporation (JP)

( * ) Notice: Subject to any disclaimer, the term of this patent is extended or adjusted under 35 U.S.C. 154(b) by 816 days.

(21) Appl. No.: 11/557,658

(22) Filed: Nov. 8, 2006

(65) Prior Publication Data

US 2007/0208539 A1 Sep. 6, 2007

Related U.S. Application Data

(62) Division of application No. 10/635,213, filed on Aug. 6, 2003, now Pat. No. 7,416,841.

(30) Foreign Application Priority Data

Aug. 7, 2002 (JP) ............................. 2002-230287

(51) Int. Cl.
*C12Q 1/68* (2006.01)
(52) U.S. Cl. ..................... 435/6; 436/518; 422/50; 422/68.1
(58) Field of Classification Search ................ None
See application file for complete search history.

(56) References Cited

FOREIGN PATENT DOCUMENTS

| | | |
|---|---|---|
| CN | 1319808 A | 10/2001 |
| JP | 08-233710 | 9/1996 |
| JP | 2002-183467 | 6/2002 |
| JP | 2002-340894 | 11/2002 |
| WO | WO 97/37218 | 10/1997 |
| WO | WO00/13018 | 3/2000 |
| WO | WO01/16860 | 3/2001 |
| WO | WO01/84150 | 11/2001 |

*Primary Examiner*—Yelena G Gakh
(74) *Attorney, Agent, or Firm*—Harness, Dickey & Pierce, P.L.C.

(57) ABSTRACT

An IJ-system reagent inspection device 3 that instructs an ejection device to eject a reagent and reads an inspection result from a detachable DNA chip module 2. The method is carried out based on inspection information of inputted inspection items to produce and output inspection data along with inputted examinee-identification information and the corresponding inspection items through communication lines. In a control device 5, the examinee identification information is received from the IJ-system reagent inspection device 3 along with the inspection items and the inspection data through the communication lines. The inspection items and the inspection data are recorded in association with the examinee identification information to request a diagnosis based on the inspection data.

6 Claims, 4 Drawing Sheets

DIAGNOSTIC ANALYTICAL METHOD UTILIZING DNA CHIPS WITH THIN-FILM TRANSISTOR (TFT) ELEMENTS

CROSS REFERENCE TO RELATED APPLICATIONS

This application is a divisional patent application of U.S. Ser. No. 10/635,213 filed Aug. 6, 2003, claiming priority to Japanese Patent Application No. 2002-230287 filed Aug. 7, 2002, all of which are incorporated by reference.

FIELD OF THE INVENTION

The present invention relates to a reagent inspection device (producing system) using an inkjet system wherein a liquid reagent is ejected on a DNA (deoxyribonucleic acid) chip module for inspection. An ejecting method (inkjet method) is used for ejecting a liquid with fluidity onto the chip module. The present invention also relates to a control device for controlling the inspection carried out by the reagent inspection device, its control method, control system, and control program.

BACKGROUND OF THE INVENTION

Recently, a DNA chip module has been used for inspecting the diagnosis of physical conditions such as genes. Using the DNA chip module, blood of an examinee and a reagent are supplied on spike spots arrayed in a matrix arrangement on the DNA chip module so as to allow them to react. An inkjet method is useful for supplying the reagent and is attracting attention.

The inspection method using the DNA chip module, however, may be achieved only by supplying blood of an examinee to the DNA chip module. As such, for people who do not have hospitals in their neighborhood, it is difficult to go to the hospital in a bad physical condition to undergo the inspection.

For this reason, it is desirable to develop an IJ-system (inkjet system) reagent inspection device, wherein a liquid reagent is ejected onto the DNA chip module for inspection, that uses a control system capable of requesting diagnosis of the inspection data from the IJ-system reagent inspection device via a communication line.

SUMMARY OF THE INVENTION

The present invention has been made in view of this desirability, and it is an object thereof to provide a control system capable of requesting a diagnosis by obtaining inspection data from an IJ-system reagent inspection device via communication lines. It is another object of the present invention to provide a reagent inspection device (producing system) using an inkjet system and its control device, control method, and control program for achieving the control system.

A reagent inspection device according to the present invention comprises an ejection device for ejecting a liquid reagent with fluidity onto an object using an inkjet system, and communicating means for transmitting and receiving data via communication lines. A connector for detachably connecting a DNA chip module, and inspecting means for instructing the ejection device to eject the reagent and reading an inspection result from the DNA chip module based on inspection information of inputted inspection items are also provided. The inspecting means also produces and outputs inspection data of the inspection result, along with any inputted examinee-identification information. The corresponding inspection items are sent through the communicating means.

DETAILED DESCRIPTION OF THE PREFERRED EMBODIMENTS

Figure 1:
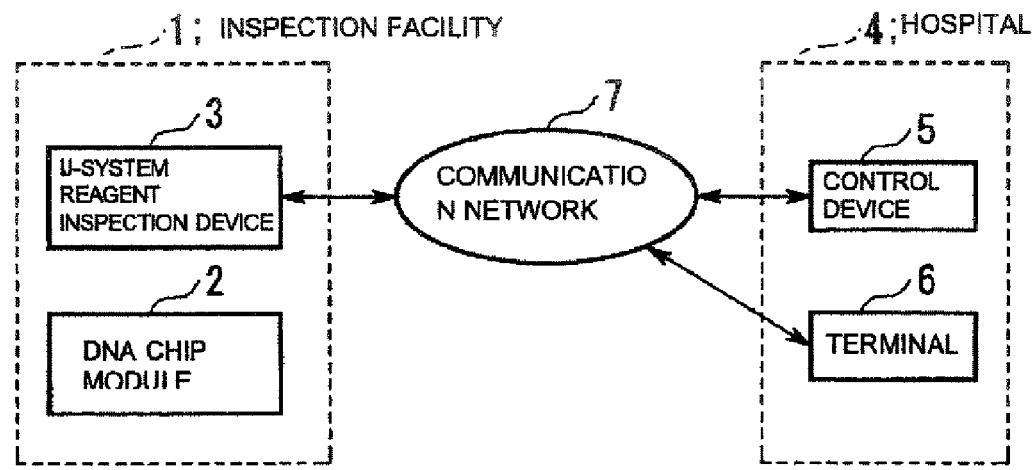
FIG. 1 is a block diagram of the entire structure of a control system of a reagent inspection device (an IJ-system reagent inspection device) using an inkjet system according to an embodiment of the present invention.

The inspecting means is characterized by recording on the DNA chip module that it is used after the inspection. The inspecting means is characterized by accessing a diagnostician database storing information of diagnosticians who diagnose using the inspection data so as to obtain and output diagnostician information so that the selectively input diagnostician information is produced and output along with the inspection data.

A control device according to the present invention comprises communicating means for transmitting and receiving data via communication lines; memorizing means for storing inspection items and their inspection data in association with examinee identification information; and control processing means for receiving the examinee identification information from a reagent inspection device along with the inspection items and the inspection data by the communicating means so as to store them in the memorizing means and to request a diagnosis based on the inspection data.

The control processing means is characterized by accessing an inspection evaluation information database storing inspection evaluation information corresponding to inspection data contents for each inspection item so as to obtain the corresponding inspection evaluation information and transmit it to the reagent inspection device through the communication means.

A control method according to the present invention comprises the steps of receiving examinee identification information along with inspection items and inspection data from a reagent inspection device through communication lines; recording the inspection items and the inspection data in association with the examinee identification information; and requesting a diagnosis based on the inspection data.

A control method according to the present invention further comprises the steps of gaining access to an inspection evaluation information database storing inspection evaluation information corresponding to inspection data contents for each inspection item so as to obtain the corresponding inspection evaluation information and transmitting the inspection evaluation information to the reagent inspection device through the communication lines.

A control program according to the present invention comprises the processes for causing a computer to execute receiving examinee identification information along with inspection items and inspection data from a reagent inspection device through communication lines; recording the inspection items and the inspection data in association with the examinee identification information; and requesting a diagnosis based on the inspection data.

A control program according to the present invention further comprises the processes for causing a computer to execute gaining access to an inspection evaluation information database storing inspection evaluation information corresponding to inspection data contents for each inspection item so as to obtain the corresponding inspection evaluation information; and transmitting the inspection evaluation information to the reagent inspection device through the communication lines.

By these control programs, the above-mentioned control device can be achieved using a computer.

A control system according to the present invention comprises a producing system, a control device, and a communication network providing communication lines capable of transmitting data, wherein the producing system and the control device are connected to the communication network.

Embodiments according to the present invention will now be described below with reference to the drawings.

FIG. 1 is a block diagram of a control system of a reagent inspection device (an IJ-system reagent inspection device) using an inkjet system. Referring to FIG. 1, an inspection facility 1 has an IJ-system reagent inspection device 3 provided therein. The inspection facility 1 is also provided with a DNA chip module 2 to be used for the inspection by the IJ-system reagent inspection device 3. Numeral 4 denotes a hospital operating the IJ-system reagent inspection device 3. The hospital 4 includes a control device 5 for controlling the inspection performed by the IJ-system reagent inspection device 3 and a terminal 6. This terminal 6 is used by a doctor in the hospital 4, for example.

Numeral 7 denotes a communication network providing communication lines capable of transmitting data. The communication network 7 may use a telephone circuit, a leased circuit, or a computer network such as the Internet, for example. The IJ-system reagent inspection device 3, the control device 5, and the terminal 6 can be connected to the communication network 7. Also, the IJ-system reagent inspection device 3 and the terminal 6 may gain access to the control device 5 via the communication network 7. For example, the control device 5 may be regarded as a server having the IJ-system reagent inspection device 3 and the terminal 6 as clients so as to form a client/server system.

Figure 2:
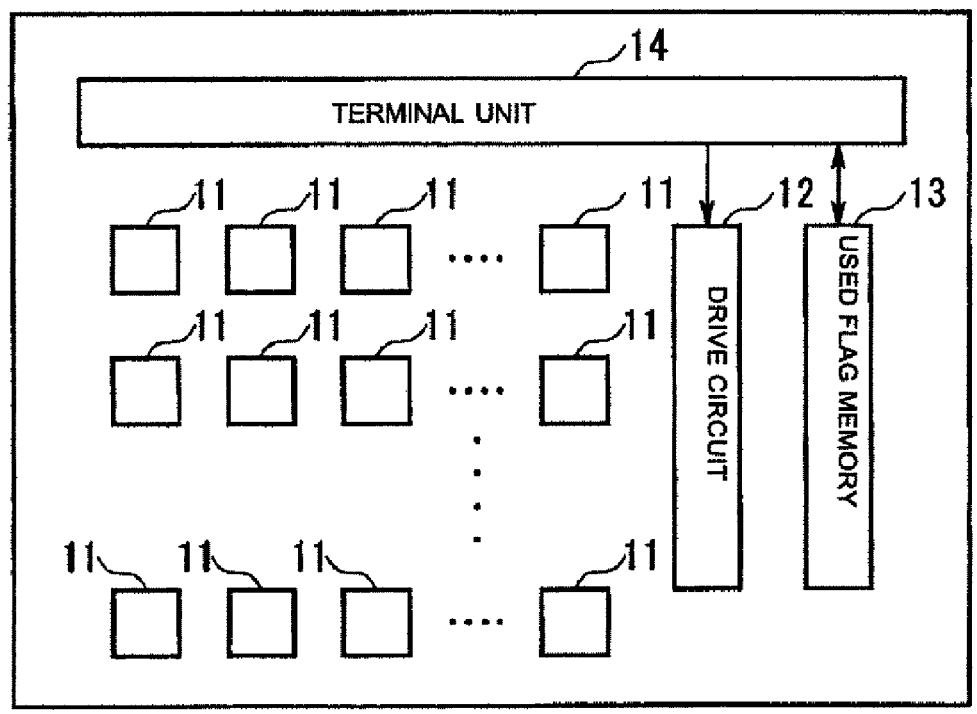
FIG. 2 is a block diagram of a structure of a DNA chip module 2 shown in FIG. 1.

FIG. 2 is a block diagram of the DNA chip module 2 shown in FIG. 1. The DNA chip module 2 is provided with a plurality of TFT elements 11 formed therein. These TFT elements 11 are substantially linearly arranged at substantially equal intervals in a plurality of lines. The TFT element 11 functions as a semiconductor field-effect biosensor for detecting the reaction between a reagent and the blood of an examinee, for example, supplied on the TFT element 11. The DNA chip module 2 also includes a drive circuit 12 for driving each TFT element 11, a used flag memory 13 for memorizing the flag showing the DNA chip module 2 being used, and a terminal unit 14 having terminals for inputting and outputting various signals during setting of the DNA chip module 2 in the IJ-system reagent inspection device 3. Through the terminal unit 14, the input or output of an output signal of each TFT element 11, an input signal to the drive circuit 12, and writing and reading signals of the used flag memory 13 are possible.

The used flag memory 13 uses a nonvolatile memory such as a flash memory. The used flag memory 13 memorizes the used flag for preventing the misuse of the DNA chip module 2 or the like. Misuse is prevented by indicating that the DNA chip module 2 is being used. In addition, since the DNA chip module 2 is treated as being non-returnable, it is preferable that the used flag memory 13 uses a non-rewritable recording element.

Figure 3:
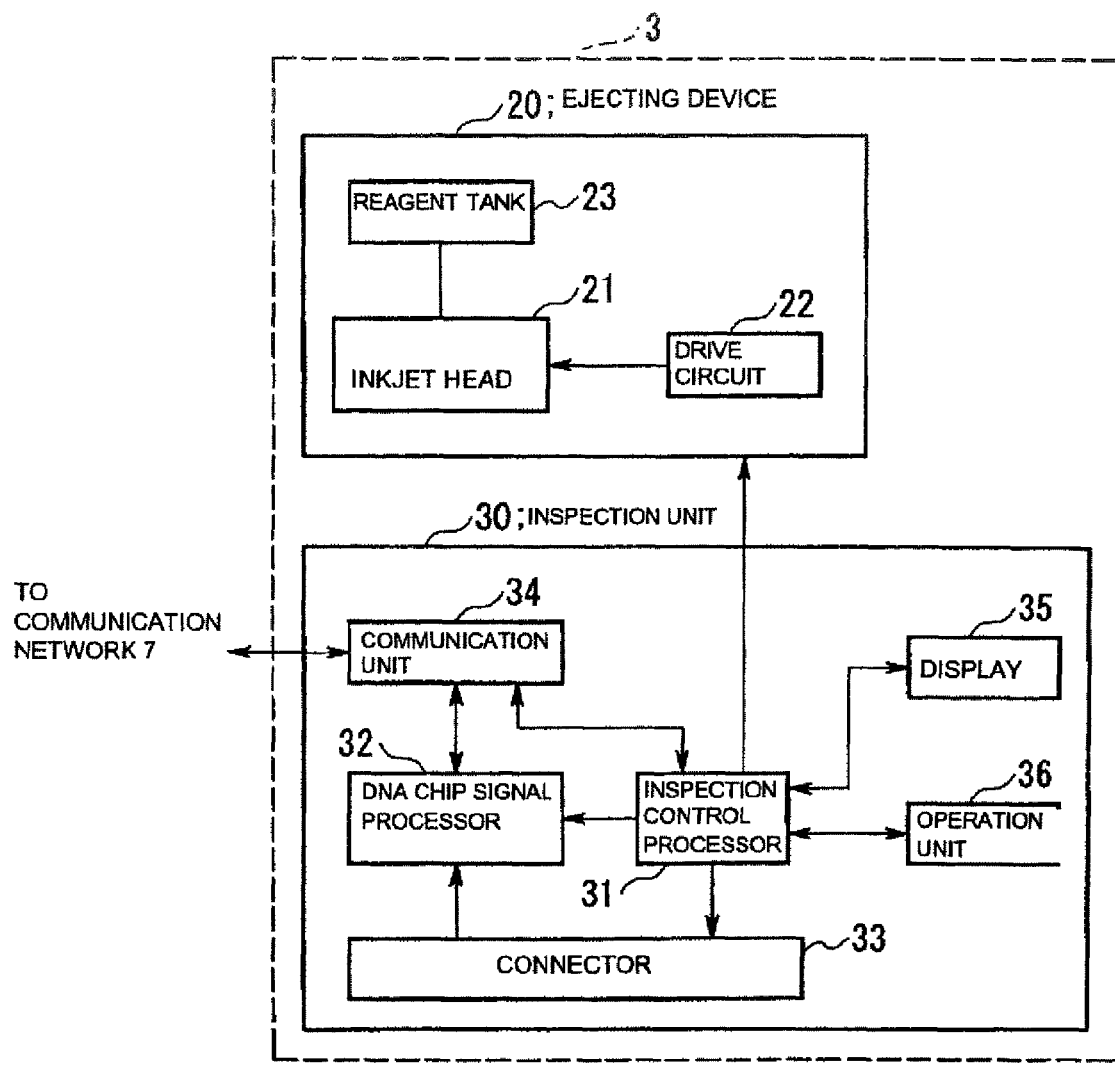
FIG. 3 is a block diagram of a structure of an IJ-system reagent inspection device 3 shown in FIG. 1.

Now referring to FIG. 3, a block diagram of the IJ-system reagent inspection device 3 shown in FIG. 1 is depicted. In FIG. 3, numeral 20 denotes an ejecting device for supplying a reagent, which is a liquid with fluidity, to the DNA chip module 2. The ejecting device 20 is composed of an inkjet head 21 for ejecting the reagent on the TFT element 11 of the DNA chip module 2 in a dot pattern by an inkjet system. The ejecting device is also composed of a driving circuit 22 for producing and outputting a driving signal for controlling the ejection operation of the inkjet head 21, a reagent tank 23 for storing the reagent to supply it to the inkjet head 21, a CPU (not shown) for controlling several parts of the circuit, and a memory (not shown) for storing the program carried out by the CPU, various data, and the like. The reagent tank 23 is a detachable structure and supplied from a reagent manufacturer with the reagent.

Numeral 30 denotes an inspection unit for inspecting the DNA chip module 2. The inspection unit 30 is composed of an inspection control processor 31 for processing the inspection control during the inspection of the DNA chip module 2, a DNA chip signal processor 32 for producing inspection data that is transmitted to the control device 5 after receiving an output signal from each TFT element 11 of the DNA chip module 2, and a connector 33 capable of connecting to the terminal unit 14 of the DNA chip module 2. The inspection unit 30 also includes a communication unit 34 that communicates data with the control device 5 by connecting to the communication network 7, a display 35 for displaying messages of the inspection, and an operation unit 36 that sets inspection items and provides instructs to execute the inspection. Through the communication unit 34, the inspection control processor 31 and the DNA chip signal processor 32 can send and receive data to and from the control device 5.

The connector 33 is structured so as to detachably attach the DNA chip module 2 thereto. Through the connector 33, the input and output signals can be sent to and from the DNA chip module 2.

The inspection control processor 31 stores inspection items and their contents, inspection procedures, reagent ejection information, and reaction times as inspection information so as to process the inspection control based on the inspection information. As the inspection control processes, the inspection control processor 31 produces and outputs a TFT-element drive designation to the drive circuit 12 of the DNA chip module 2 according to the inspection procedure established by the operation unit 36. The drive circuit 12 drives the TFT element 11 according to the TFT-element drive designation. Also, the used flag memory 13 is read and written.

The inspection control processor 31 also informs the ejecting device 20 of reagent ejection information corresponding to the inspection item established by the operation unit 36 so as to instruct the ejecting device 20 to execute ejection. The reagent ejection information may be a discharge rate of the reagent, for example, and the discharge rate is stored for each TFT element 11 of the DNA chip module 2. On the basis of the reagent ejection information, the ejecting device 20 adjusts the discharge rate for each TFT element 11.

The DNA chip signal processor 32 stores process information for producing inspection data. The output signal of each TFT element 11 received from the DNA chip module 2 based on this process information. Also, when the inspection data is sent to the control device 5, examinee identifying information and inspection items established by the operation unit 36 are sent along therewith. This examinee identifying information is identifiable as a health insurance ID card number, or a patient's file number at the hospital 4, for example.

The inspection information is renewable from the control device 5 via the communication network 7. Also, the contents of the inspection data producing process carried out by the DNA chip signal processor 32 is renewable from the control device 5 in the same way.

In addition, the functions of the inspection control processor 31 and the DNA chip signal processor 32 may be achieved by using dedicated hardware, or their functions may be achieved by loading programs into the memories and CPUs (central processing units) of the processors.

Figure 4:
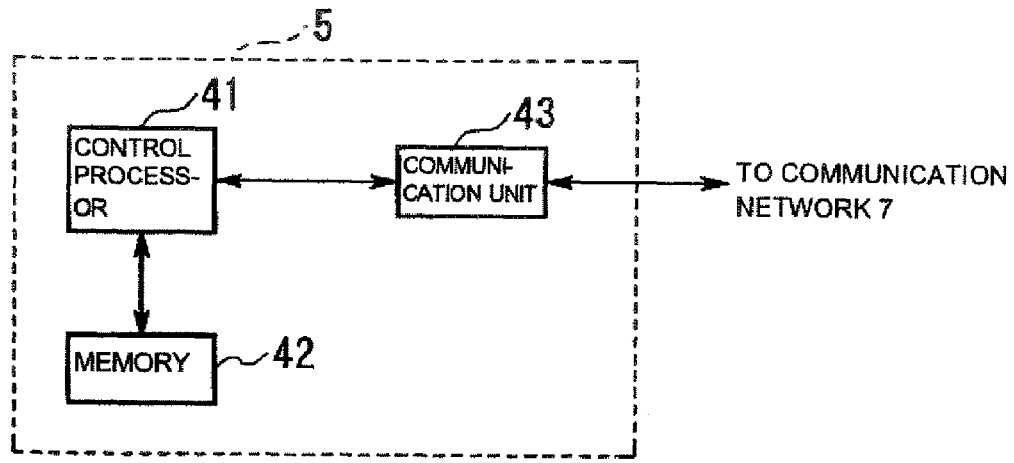
FIG. 4 is a block diagram of a structure of a control device 5 shown in FIG. 1.

FIG. 4 is a block diagram of the control device 5 shown in FIG. 1. In FIG. 4, numeral 41 denotes a control processor that controls the inspection carried out by the IJ-system reagent inspection device 3. Numeral 42 denotes a memory for storing various data and this memory is accessible from the control processor 41. Numeral 43 denotes a communication unit that communicates data with the IJ-system reagent inspection device 3 or the terminal 6 by connecting with the communication network 7. Using the communication unit 43, the control processor 41 can send and receive data to and from the IJ-system reagent inspection device 3 and the terminal 6.

It is preferable that an input device and a display (both not shown) are also connected, as peripheral devices, to the control device 5. The input device is preferably a keyboard or a mouse, and the display means is preferably a CRT (cathode ray tube), a liquid crystal display, or the like.

The control processor 41 records the inspection items and their inspection data that are received from the IJ-system reagent inspection device 3 on the memory 42. The control processor 41 records the inspection items and their inspection data by relating them to the corresponding examinee identifying information that is received along with the inspection items and their inspection data. Also, in the memory 42, information that identifies persons who are permitted to gain access to the control device 5 is stored. This information could be a user-ID and its password, for example. When trying to gain access, the control processor 41 requires inputting a user-ID and its password which permits access only when they agree with the user ID and its password stored in the memory 42. In this manner, the leaking of personal information of an examinee from being is prevented.

Also in the memory 42, diagnosis-request destination information that requests the diagnosis of inspection data is stored for each inspection item. The control processor 41 sends a diagnosis-request notification to the corresponding diagnosis-request destination based on diagnosis-request destination information that corresponds to an inspection item received along with inspection data. Examples of this diagnosis-request destination information may be an IP (internet protocol) address of the terminal 6 used by a diagnosing doctor, or an E-mail address of the diagnosing doctor.

In addition, the functions of the control processor 41 may be achieved by using dedicated hardware, or their functions may also be achieved by loading programs into the memory and CPU (central processing unit), of the processor.

Figure 5:
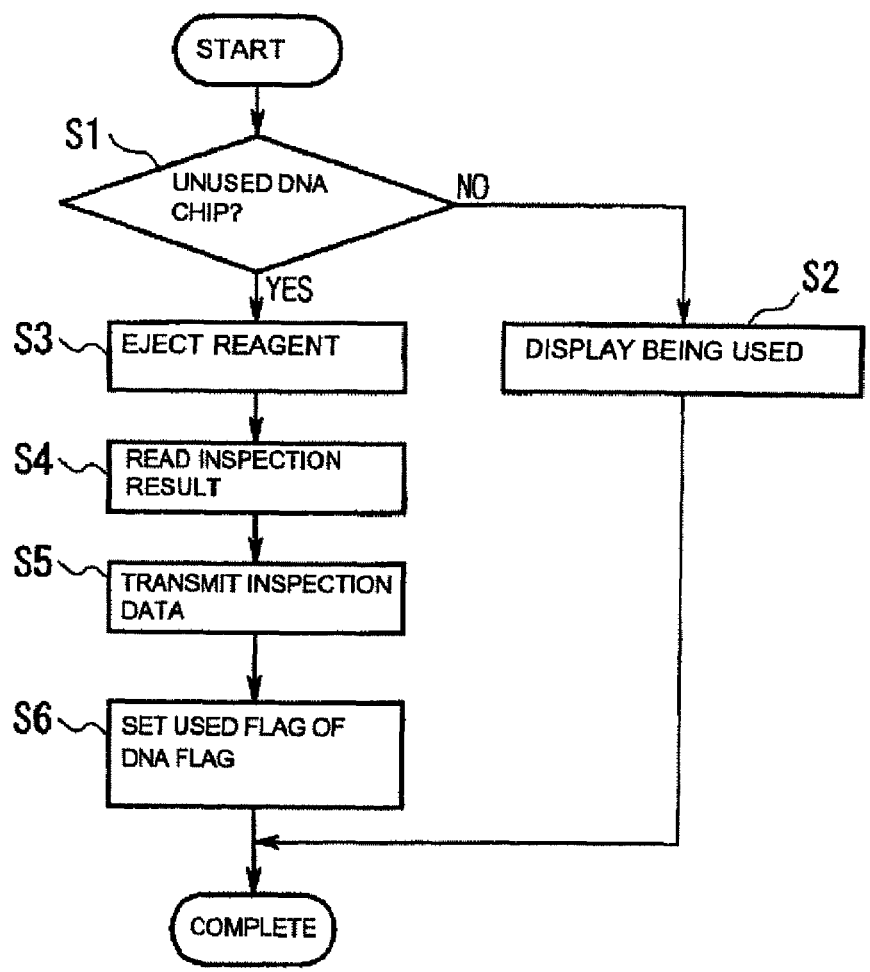
FIG. 5 is a flowchart of a flow of the inspection processing carried out by the IJ-system reagent inspection device 3 shown in FIG. 3.

Next, referring to FIG. 5, operation during inspection in the inspection facility 1 will be described. FIG. 5 is a flowchart of the inspection process carried out by the IJ-system reagent inspection device 3 shown in FIG. 3. First, an inspector in the inspection facility 1 supplies blood of an examinee, for example, to each TFT element 11 of the DNA chip module 2 by setting the DNA chip module 2 in the connector 33 of the IJ-system reagent inspection device 3. This initiates inspection by the operation unit. Then, the inspector selects a target inspection item from inspection items displayed on the display 35, and also inputs examinee identifying information. In addition, when the inspection item is selected, the inspection content of each inspection item may also be displayed.

Next, the inspection control processor 31 of the IJ-system reagent inspection device 3 reads a used flag from the used flag memory 13 of the DNA chip module 2 so as to confirm whether the used flag is unset (unused state). When the used flag is set (used state), a message that the corresponding DNA chip module 2 is used is displayed on the display 35 so as to finish the processing (steps S1 and S2 in FIG. 5).

On the other hand, if the used flag is unset so that the DNA chip module 2 is unused, the inspection control processor 31 informs the ejecting device 20 of the reagent ejection information corresponding to each of the established inspection items so as to instruct to execute the ejection. Thereby, the ejecting device 20 ejects the reagent on each TFT element 11 while adjusting the ejection amount of the reagent for each TFT element 11 based on the reagent ejection information (step S3).

Next, the inspection control processor 31 instructs the drive circuit 12 of the DNA chip module 2 to drive the TFT element according to the corresponding inspection procedure. After a reaction period, the inspection result from the DNA chip module 2 is read. The inspection control processor 31 also instructs the DNA chip signal processor 32 to produce the inspection data from the output signals of each TFT element 11 received from the DNA chip module 2. In this manner, the drive circuit 12 drives the corresponding TFT element 11 according to the TFT element driving instructions so that the DNA chip signal processor 32 receives the output signal produced by the TFT element 11 so as to produce the inspection data (step S4).

Next, the DNA chip signal processor 32 sends the produced inspection data to the control device 5 through the communication unit 34. The examinee identifying information and the inspection items established by the operation unit 36 are also sent (step S6). Further, the inspection control processor 31 writes the used flag in the used flag memory 13 to set it in a used state (step S6). In this manner, the inspection processing carried out by the IJ-system reagent inspection device 3 is finished.

Figure 6:
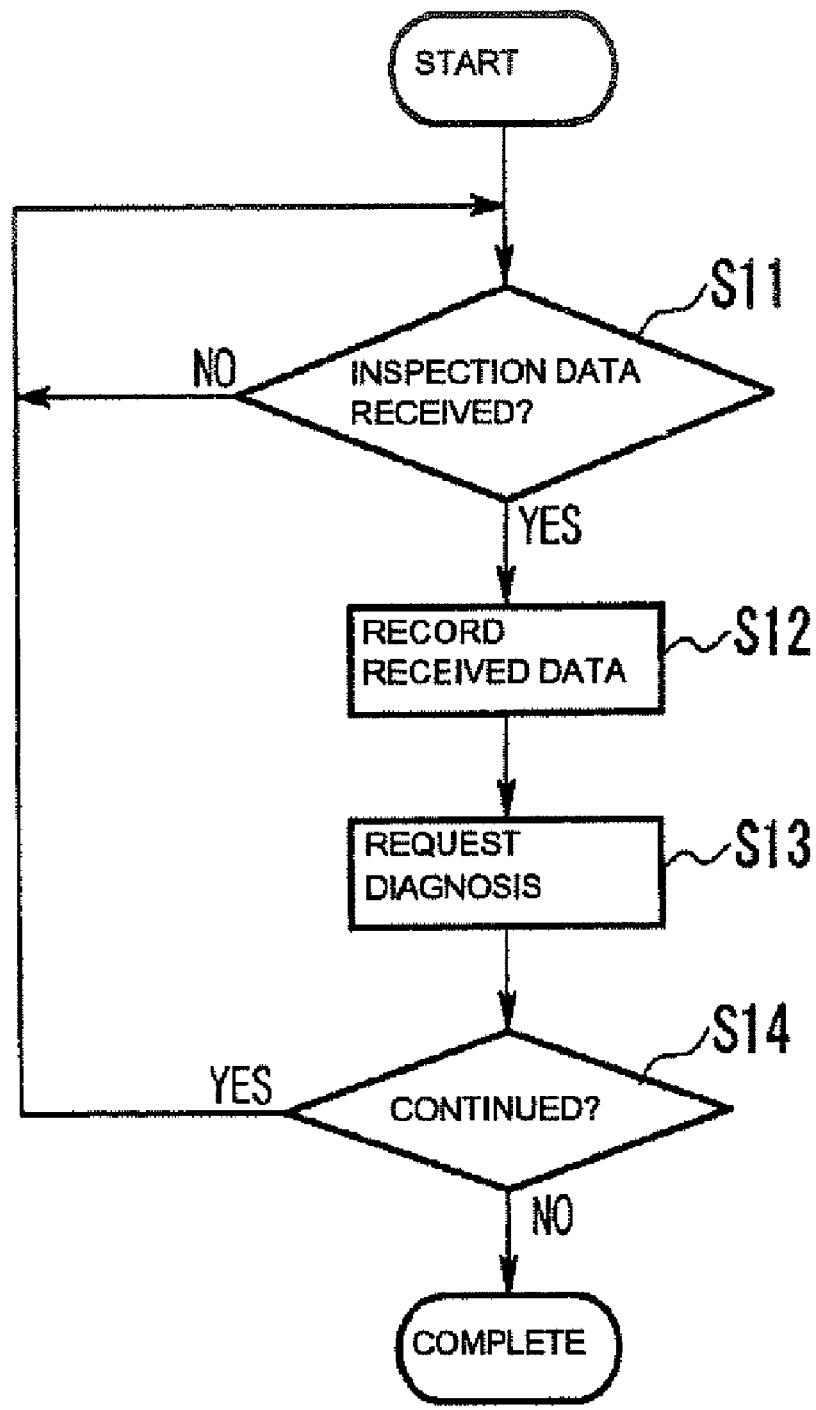
FIG. 6 is a flowchart of a flow of the control processing carried out by a control processor 41 shown in FIG. 4.

Now, referring to FIG. 6, the operation of the control device 5 at the hospital 4 where the inspection data is received will be described. FIG. 6 is a flowchart of the control processing carried out by the control processor 41 shown in FIG. 4. First, upon receiving inspection items and inspection data from the IJ-system reagent inspection device 3 through the communication unit 43, the control device 5 records the corresponding inspection items and the inspection data on the memory 42. This is done by relating the inspection items and inspection data with the examinee identifying information received (steps S11 and S12 shown in FIG. 6). Then, the control processor 41 sends a diagnosis-request notification to a corresponding diagnosis-request destination based on the diagnosis-request destination information that is received along with inspection data (step S13). The diagnosis-request destination information corresponds to a selected inspection item. Thereafter, if the processing is continued, the process is returned to the step S11.

The doctor who has received the diagnosis-request notification obtains the inspection data by accessing the control device 5 through the terminal 6 in order to diagnose the corresponding inspection item. The diagnosis result is then sent to the examinee via a confidential mail or an E-mail with a password. In this manner, personal information of the examinee is protected.

In addition, according to the embodiment described above, an examinee may select a diagnostician. For example, during an inspection in the inspection facility 1 that has a diagnostician database that stores diagnostician (doctor) information, a list of diagnosticians demanded by an examinee may be obtained from the IJ-system reagent inspection device 3 by accessing the diagnostician database. Then, the diagnostician information selected by the examinee is sent to the control device 5 along with the inspection data. The control device 5 requests a diagnosis by the diagnostician shown in the diagnostician information. In this manner, the examinee can simply select a doctor, such as a family doctor, that will request the diagnosis.

Also, by providing an inspection assessment information database that stores inspection assessment information corresponding to the content of the inspection data for each inspection item (decision information of suspicious diseases and symptoms, for example), when the control device 5 receives the inspection data, the corresponding inspection assessment information may be obtained by accessing the inspection assessment information database. The inspection assessment information may then be sent to the IJ-system reagent inspection device 3 and displayed. In this manner, the information based on the inspection can be promptly sent to the examinee after the inspection. As a result, the examinee can be made aware of physical conditions detected by the inspection promptly after the inspection.

Furthermore, if the past inspection data, diagnosis results, and symptoms for each examinee are stored in the inspection assessment information database, more precise information can be given to the examinee.

In addition, according to the embodiment described above, the inspection information may be stored in the inspection control processor 31 of the IJ-system reagent inspection device 3, or it may be recorded in the control device 5 so that the corresponding inspection information may be accessed at the control device 5 through the IJ-system reagent inspection device 3. Alternatively, the inspection information may be stored in a database different from the control device 5.

Also, according to the embodiment described above, when the inspection result is read from the DNA chip module 2, the output signal of the TFT element 11 is obtained to produce the inspection data. It should be understood, however, that the inspection result may be read by other methods. For example, various reaction situations on the TFT element 11 may be obtained optically by a CCD (charge coupled device) as image data to produce the inspection data. Also, the inspection data may be processed by the control device 5.

In addition, according to the embodiment described above, the DNA chip module may have a semiconductor field-effect biosensor formed on the TFT element. Alternatively, the DNA chip module may have a semiconductor field-effect biosensor formed on another element that is different from the TFT element. That is, the biosensor may be another sensor than the semiconductor field-effect biosensor.

Further, the arrangement of the biosensor on the DNA chip module should not be limited to the arrangement in the above embodiment in that the elements may be substantially linearly arranged at substantially equal intervals in a plurality of lines.

Also, according to the embodiment described above, the inkjet head 21 provided in the ejecting device 20 may be an inkjet head structured to eject ink using the deflection of a piezoelectric element. Further, the inkjet head may be an inkjet head with a structure such as an ink-ejecting system that uses bubbles produced by heating, for example.

Also, in the inkjet head 21, the nozzles may be substantially linearly arranged at substantially equal intervals in a plurality of lines. Alternatively, the nozzles may not be at equal intervals, or the nozzles may not be linearly arranged in lines.

The inspection processing may be carried out by using recording programs that achieve the processing carried out by the IJ-system reagent inspection device 3 shown in FIG. 3 on a computer-readable recording medium. In this manner, a computer system can read and execute the programs recorded on the recording medium.

The control processing may also be carried out by using recording programs that achieve the processing carried out by the control device 5 shown in FIG. 4 on a computer-readable recording medium. Again, this causes the computer system to read and execute the programs recorded on the recording medium.

In addition, "the computer system" here may include an OS (operating system) and hardware such as peripheral devices. Also, "the computer system" may include a Web site providing environment (or display environment) if a WWW (world wide web) system is used. Further, "the computer-readable recording medium" may be represented by a portable medium such as a flexible disk, a magnetic-optical disk, an ROM (read only memory), a CD-ROM (compact disk read only memory), and a memory device such as a hard disk built in a computer system.

Furthermore, "the computer-readable recording medium" may include a device that holds a program for a predetermined period of time such as a volatile memory (RAM random access memory) in a computer system. This serves as a server or client when a program is transmitted over a network such as the Internet, or communication lines such as a telephone circuit.

Also, the above-mentioned program may be transmitted from a computer system housing the program in a memory to another computer system via a transmission medium, or through a transmitted wave in the transmission medium. The "transmission medium" transmitting the program represents a medium that has an information-transmitting function such as a network (communication network) or communication lines (communication wire). An example of a network would be the Internet, and an example of a communication line would be a telephone circuit.

Furthermore, the program may also used in combination with a program having the above-mentioned functions already recorded in the computer system, which is a so-called difference file (difference program).

It should be understood that although the embodiments according to the present invention have been described above in detail, a specific structure is not limited to the above embodiments and may be modified in accordance with the spirit and scope of the invention.

As described above, according to the present invention, the reagent inspection device (IJ-system reagent inspection device) uses an inkjet system and gives instructions to eject a reagent to the ejection device. The reagent inspection device also reads an inspection result received from the detachable DNA chip module. The inspection result is based on inspection information of the inputted inspection items that is produced and output as inspection data along with inputted examinee-identification information and the corresponding inspection items through communication lines.

In the control device, the examinee identification information is received from the reagent inspection device along with the inspection items and inspection data through communication lines. The inspection items and the inspection data are recorded in association with the examinee identification information to request a diagnosis based on the inspection data. In this manner, if the IJ-system reagent inspection device and the control device are connected to the communication network, a control system can be provided which is capable of receiving the inspection data from the IJ-system reagent inspection device via the communication lines.

As a result, if the IJ-system reagent inspection devices are placed in scattered facilities such as convenience stores, a number of people can freely undergo an inspection. As such, the device contributes an advantage to the health care of many people. In particular, for people who do not have hospitals in their neighborhood, the device of the present invention is very useful because they can immediately go through an inspection in a bad physical condition which requires attention immediately.

Further, in the IJ-system reagent inspection device and after the inspection, the DNA chip module is recorded as having been used so that errors such as using the used DNA chip module in another inspection can be prevented.

Also, by accessing an inspection evaluation information database that stores information about diagnosticians who diagnose the inspection data, one can obtain and output the desired diagnostician information. In this manner, the selectively inputted diagnostician information may be produced along with the inspection data, so that an examinee can select a diagnostician such as a home doctor to request a diagnosis.

Moreover, by accessing an inspection evaluation information database that stores inspection evaluation information which corresponds to the inspection data contents for each inspection item, the corresponding inspection evaluation information may be obtained and transmitted to the reagent inspection device. In this manner, the information based on the inspection can be promptly sent to the examinee after the inspection.

What is claimed is:

1. A control method comprising the steps of:
   receiving examinee identification information along with analytical parameters and inspection data through a communicating network for transmitting and receiving data via communication lines from a reagent inspection device including a removable DNA chip module having a plurality of thin-film transistor (TFT) elements, a drive circuit for driving each TFT element, a used flag memory, a terminal unit, and an ejection device for ejecting the liquid reagent onto the DNA chip module, the TFT elements being substantially linearly arranged at substantially equal intervals in a plurality of lines and functioning as semiconductor field-effect biosensors for detecting the reaction between a liquid reagent and the blood of an examinee supplied on the TFT elements;
   recording the analytical parameters and the inspection data in association with the examinee identification information with an analysis unit that stores the analytical parameters, receives the examinee identification information, instructs the ejection device to eject the reagent to the DNA chip module, reads results of an analyzed DNA chip module based on selected analytical parameters, and produces and outputs data related to the results of the analyzed DNA chip module; and
   requesting a diagnosis based on the inspection data,
   wherein the analysis unit produces and outputs the data of the results of the analyzed DNA chip module, the examinee-identification information, and the selected analytical parameters through the communicating network;
   the analysis unit is adapted to be controlled from a remote location through the communicating network by a control unit such that the analytical parameters may be selected remotely via the communication network;
   the analytical parameters are information directed to diseases and symptoms; and
   the terminal unit includes terminals for inputting and outputting various signals of each TFT element, is adapted to input a signal to the drive circuit, and is adapted to write and read signals of the used flag memory.

2. The method according to claim 1, further comprising recording on the DNA chip module that the DNA chip module has been used after the analysis with the analysis unit.

3. The method according to claim 1, further comprising accessing a diagnostician database that stores information of diagnosticians who diagnose the data of the results of the inspected DNA chip module; and
   obtaining and outputting diagnostician information obtained from the diagnostician database so that the selected diagnostician information is produced along with the data of the results of the inspected DNA chip module with the analysis unit.

4. A computer readable storage medium including a control program comprising the processes for causing a computer to execute:
   receiving examinee identification information along with analytical parameters and inspection data through a communicating network for transmitting and receiving data via communication lines from a reagent inspection device including a removable DNA chip module having a plurality of thin-film transistor (TFT) elements, a drive circuit for driving each TFT element, a used flag memory, a terminal unit, and an ejection device for ejecting the liquid reagent onto the DNA chip module, the TFT elements being substantially linearly arranged at substantially equal intervals in a plurality of lines and functioning as semiconductor field-effect biosensors for detecting the reaction between a liquid reagent and the blood of an examinee supplied on the TFT elements;
   recording the analytical parameters and the inspection data in association with the examinee identification information with an analysis unit that stores the analytical parameters, receives the examinee identification information, instructs the ejection device to eject the reagent to the DNA chip module, reads results of an analyzed DNA chip module based on selected analytical parameters, and produces and outputs data related to the results of the analyzed DNA chip module; and
   requesting a diagnosis based on the inspection data,
   wherein the analysis unit produces and outputs the data of the results of the analyzed DNA chip module, the examinee-identification information, and the selected analytical parameters through the communicating network;
   the analysis unit is adapted to be controlled from a remote location through the communicating network by a control unit such that the analytical parameters may be selected remotely via the communication network;
   the analytical parameters are information directed to diseases and symptoms; and
   the terminal unit includes terminals for inputting and outputting various signals of each TFT element, is adapted to input a signal to the drive circuit, and is adapted to write and read signals of the used flag memory.

5. The medium according to claim 4, further comprising recording on the DNA chip module that the DNA chip module has been used after the analysis with the analysis unit.

6. The medium according to claim 4, further comprising accessing a diagnostician database that stores information of diagnosticians who diagnose the data of the results of the inspected DNA chip module; and
   obtaining and outputting diagnostician information obtained from the diagnostician database so that the selected diagnostician information is produced along with the data of the results of the inspected DNA chip module with the analysis unit.

* * * * *